United States Patent
Steele et al.

(10) Patent No.: US 10,517,632 B2
(45) Date of Patent: Dec. 31, 2019

(54) TISSUE-REMOVING CATHETER WITH RECIPROCATING TISSUE-REMOVING HEAD

(71) Applicant: Covidien LP, Mansfield, MA (US)

(72) Inventors: Bradley Steele, Plymouth, MN (US); Cassandra Morris, Plymouth, MN (US); William Whealon, Chaska, MN (US); Thomas McPeak, Shakopee, MN (US)

(73) Assignee: Covidien LP, Mansfield, MA (US)

( * ) Notice: Subject to any disclaimer, the term of this patent is extended or adjusted under 35 U.S.C. 154(b) by 396 days.

(21) Appl. No.: 15/188,525

(22) Filed: Jun. 21, 2016

(65) Prior Publication Data

US 2016/0374717 A1 Dec. 29, 2016

Related U.S. Application Data

(60) Provisional application No. 62/184,278, filed on Jun. 25, 2015.

(51) Int. Cl.
*A61B 17/32* (2006.01)
*A61B 17/3207* (2006.01)
*A61B 17/00* (2006.01)

(52) U.S. Cl.
CPC ......... *A61B 17/320758* (2013.01); *A61B 2017/00685* (2013.01); *A61B 2017/320716* (2013.01); *A61B 2017/320775* (2013.01)

(58) Field of Classification Search
CPC .......................................... A61B 17/320758; A61B 2017/320028; A61B 2017/320716; A61B 2017/320775
See application file for complete search history.

(56) References Cited

U.S. PATENT DOCUMENTS

| | | | |
|---|---|---|---|
| 4,749,376 A | 6/1988 | Kensey et al. | |
| 4,854,325 A | 8/1989 | Stevens | |
| 4,994,067 A | 2/1991 | Summers | |
| 5,071,425 A | 12/1991 | Gifford, III et al. | |
| 5,116,350 A | 5/1992 | Stevens | |
| 5,195,956 A | 3/1993 | Stockmeier | |
| 5,234,451 A | 8/1993 | Osypka | |
| 5,250,059 A | 10/1993 | Andreas et al. | |
| 5,366,464 A | 11/1994 | Belknap | |
| 5,372,601 A | 12/1994 | Lary | |
| 5,423,799 A * | 6/1995 | Shiu ............... | A61B 17/320758 606/159 |
| 5,431,673 A | 7/1995 | Summers et al. | |
| 5,624,457 A * | 4/1997 | Farley ............. | A61B 17/320783 606/159 |
| 5,632,755 A * | 5/1997 | Nordgren ........ | A61B 17/32075 604/22 |

(Continued)

OTHER PUBLICATIONS

International Search Report and Written Opinion for PCT Application No. PCT/US2016/038819, dated Sep. 2, 2016, 14 pages.

*Primary Examiner* — Alexander J Orkin

(57) ABSTRACT

A tissue-removing catheter includes a catheter body and a tissue-removing head. The catheter body has an annular shearing blade at the distal end thereof. The tissue-removing head is at the distal end of the catheter body and is configured to rotate about an head axis relative to the catheter body, and reciprocate along the head axis relative to the catheter body between proximal and distal positions.

21 Claims, 8 Drawing Sheets

(56) References Cited

U.S. PATENT DOCUMENTS

| | | | |
|---|---|---|---|
| 5,653,696 A * | 8/1997 | Shiber | A61B 17/22012 604/267 |
| 5,882,329 A * | 3/1999 | Patterson | A61B 17/3207 604/500 |
| 6,027,450 A * | 2/2000 | Brown | A61B 17/320758 600/159 |
| 6,554,846 B2 | 4/2003 | Hamilton et al. | |
| 6,951,566 B2 | 10/2005 | Lary | |
| 7,008,381 B2 * | 3/2006 | Janssens | A61B 10/0233 600/564 |
| 2002/0058956 A1 * | 5/2002 | Honeycutt | A61B 17/320758 606/159 |
| 2002/0138091 A1 * | 9/2002 | Pflueger | A61B 10/0266 606/170 |
| 2003/0083681 A1 * | 5/2003 | Moutafis | A61B 17/1617 606/167 |
| 2005/0113853 A1 * | 5/2005 | Noriega | A61B 17/320758 606/159 |
| 2005/0165430 A1 * | 7/2005 | Kono | A61B 17/22 606/159 |
| 2006/0229646 A1 * | 10/2006 | Sparks | A61B 17/320758 606/159 |
| 2008/0125798 A1 * | 5/2008 | Osborne | A61B 17/221 606/159 |
| 2009/0024085 A1 | 1/2009 | To et al. | |
| 2009/0138031 A1 * | 5/2009 | Tsukernik | A61B 17/320758 606/159 |
| 2009/0216180 A1 | 8/2009 | Lee et al. | |
| 2010/0125253 A1 | 5/2010 | Olson et al. | |
| 2012/0071907 A1 | 3/2012 | Pintor et al. | |
| 2012/0109171 A1 * | 5/2012 | Zeroni | A61B 17/320758 606/159 |
| 2014/0316450 A1 | 10/2014 | Higgins | |
| 2014/0350582 A1 | 11/2014 | Higgins | |
| 2015/0150590 A1 | 6/2015 | Zeroni et al. | |

* cited by examiner

TISSUE-REMOVING CATHETER WITH RECIPROCATING TISSUE-REMOVING HEAD

CROSS-REFERENCE TO RELATED APPLICATIONS

The present application claims the benefit of U.S. Provisional Ser. No. 62/184,278, filed Jun. 25, 2015, the entirety of which is hereby incorporated by reference.

FIELD OF THE DISCLOSURE

The present disclosure generally relates to a tissue-removing catheter with a reciprocating tissue-removing head.

BACKGROUND OF THE DISCLOSURE

Diseased body lumens may include an occlusion that completely or substantially completely block flow within the lumen. For example, Chronic Total Occlusions (CTOs) are vascular lesions which totally occlude a blood vessel and thereby inhibit normal blood flow. Such occlusions can occur anywhere in a patient's vascular system, arteries, and veins, including coronary vessels, as well as carotid arteries, renal arteries, cerebral arteries, arteries of the head and neck, iliac arteries, femoral arteries, popliteal arteries, and other peripheral arteries. One method of treating CTOs includes the use of a tissue-removing device to restore the patency of the vessel. However, there are challenges in treating CTOs using current devices.

SUMMARY OF THE DISCLOSURE

A tissue-removing catheter includes a catheter body with an annular shearing blade, and a tissue-removing head that both rotates about an head axis and reciprocates along the head axis. The tissue-removing head reciprocates between a proximal position, in which the tissue-removing head is adjacent the annular shearing blade, and a distal position, in which the tissue-removing head is spaced axially from the annular shearing blade.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
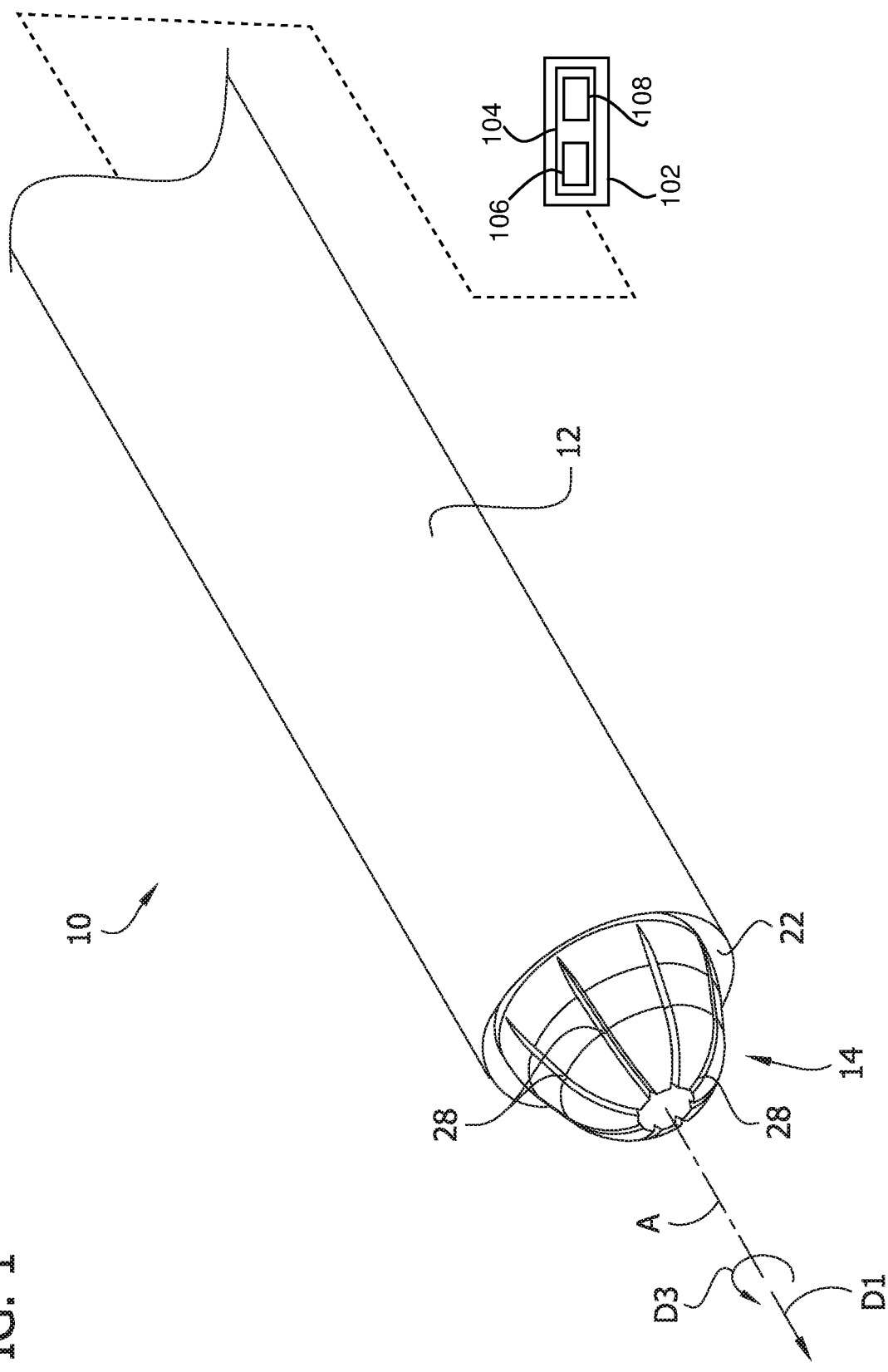
FIG. 1 is an enlarged, partial perspective of an illustrated embodiment of a tissue-removing catheter, a tissue-removing head of the catheter being in a proximal position.
Figure 2:
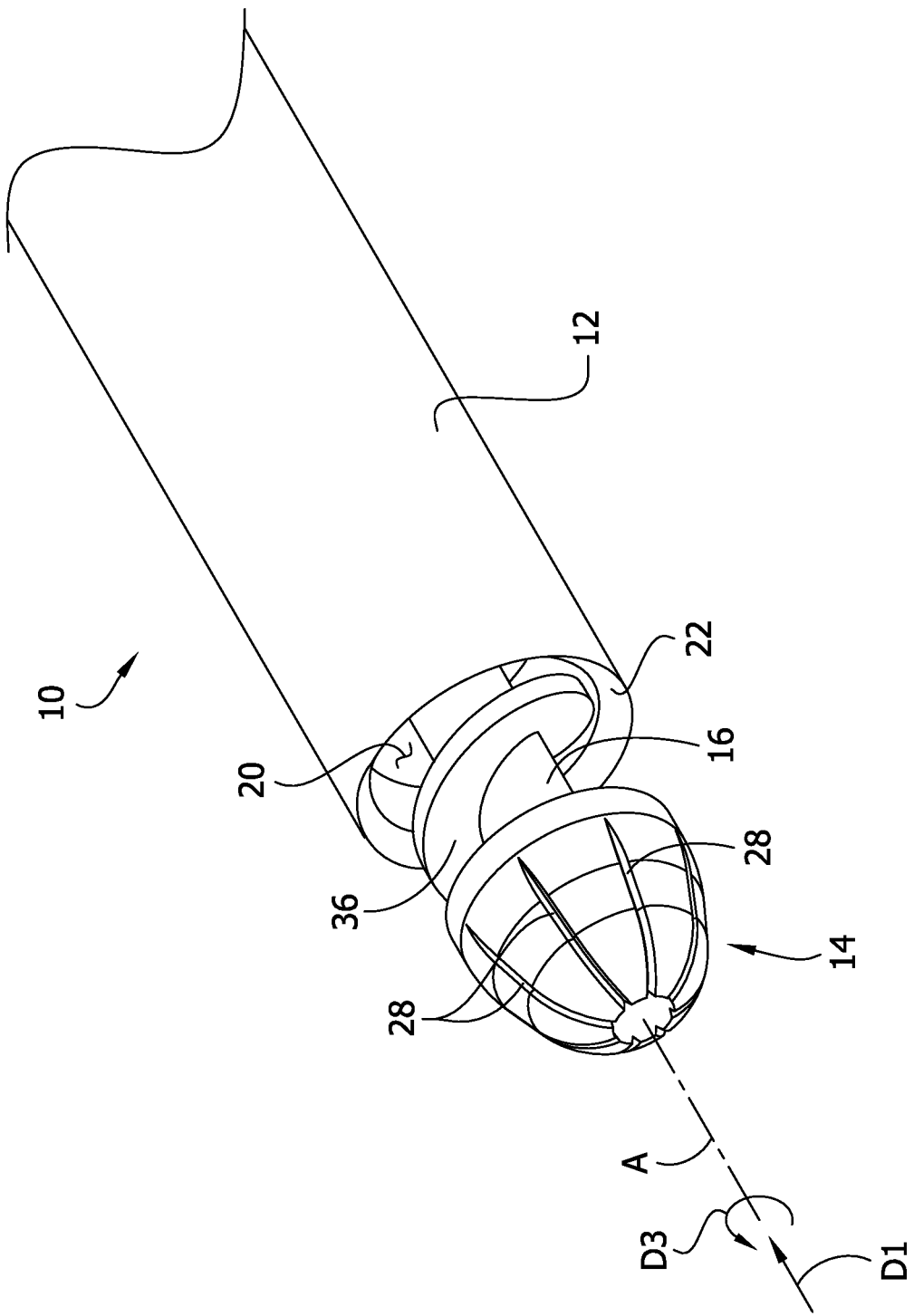
FIG. 2 is similar to FIG. 1 with the tissue-removing head in a distal position.

Referring to FIGS. 1 and 2 of the drawings, one embodiment of a tissue-removing catheter for removing tissue from a body lumen is generally indicated at reference numeral 10. The illustrated tissue-removing catheter 10 is particularly suitable for removing tissue (e.g., plaque) from an occlusion that has totally occluded the body lumen in order to restore the patency of the lumen. In one particular example, the catheter 10 is suitable for removing tissue from a chronic total occlusion (CTO) in a vascular lumen (e.g., an artery).

The catheter 10 comprises a catheter body 12, a tissue-removing head, generally indicated at 14, at a distal end of the catheter body, and a rotatable driveshaft 16 operatively connected to the tissue-removing head for both rotating the tissue-removing head about head axis A and reciprocating the tissue-removing head along the head axis A. As explained in more detail below, the tissue-removing head 14 extends distally outward from the distal end of the catheter body 12 and alternates between moving in a distal direction (indicated by arrow D1) from a proximal position relative to the catheter body (FIG. 1) to a distal position (FIG. 2), and moving in a proximal direction (indicated by arrow D2) from the distal position to the proximal position (FIG. 2). The tissue-removing head 14 reciprocates in this way simultaneously with rotating about the head axis A in a cutting direction (indicated by arrow D3).

The catheter body 12 is elongate and at least a longitudinal portion thereof is generally flexible to allow the catheter body to navigate generally tortious body lumens. The catheter body 12 is generally tubular defining an inner lumen 20 (FIGS. 3-5) extending along the catheter body in which the driveshaft 16 extends. A shearing blade 22 disposed at the distal end of the catheter body 12 shears tissue entering the inner lumen 20 during a tissue-removing operation of the catheter 10, as explained below. The illustrated shearing blade 22 has an annular shape with an inner opening partially defining the inner lumen. The catheter body 12 may comprise a torque tube including a coiled metal wire with plastic laminated over the coiled metal wire. A hypotube may be attached to a distal end of the torque tube. The hypotube may include the shearing blade 22 and may be formed from nitinol, stainless steel, carbide, cobalt chrome, MP35N, titanium, or high strength engineering plastic (e.g., radel, PEEK, delrin). The catheter body 12 may have other configurations and may be formed in other ways.

As shown in FIGS. 1 and 2 and other drawings, the illustrated tissue-removing head 14 has a generally conical or dome-shape that tapers distally and is suitable for boring through tissue (e.g., plaque) occluding a body lumen. The tissue-removing head 14 includes a plurality of flutes 28, which in the illustrated embodiments are straight or linear as opposed to helical. The flutes 28 extend from a distal end toward a proximal end of the tissue-removing head and are spaced apart from one another around the head axis A. The flutes 28 define cutting edges that engage and remove tissue as the tissue-removing head 14 rotates and reciprocates about and along the head axis A. The tissue-removing head 14 may also have an abrasive exterior surface for abrading the tissue. For example, an abrasive material may be applied to the exterior surface of the tissue-removing head 14 or the exterior surface may otherwise be formed to be abrasive. The tissue-removing head 14 may be formed from metal or other suitable material. The tissue-removing head may be of other configurations without departing from the scope of the present invention.

Figure 3:
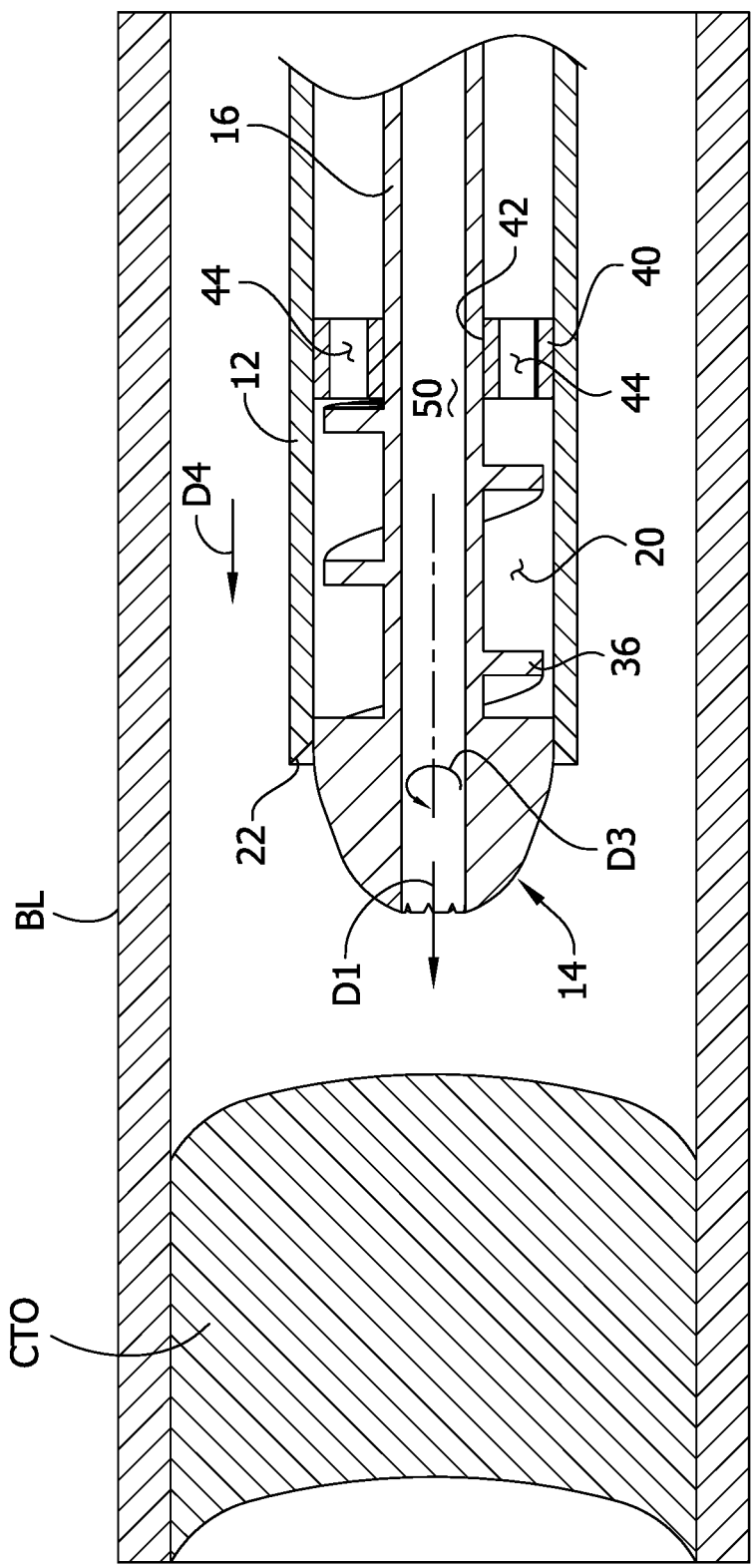
FIG. 3 is an enlarged cross section of a distal end portion of the catheter received in a body lumen adjacent a Chronic Total Occlusion (CTO), the tissue-removing head being in the proximal position.
Figure 4:
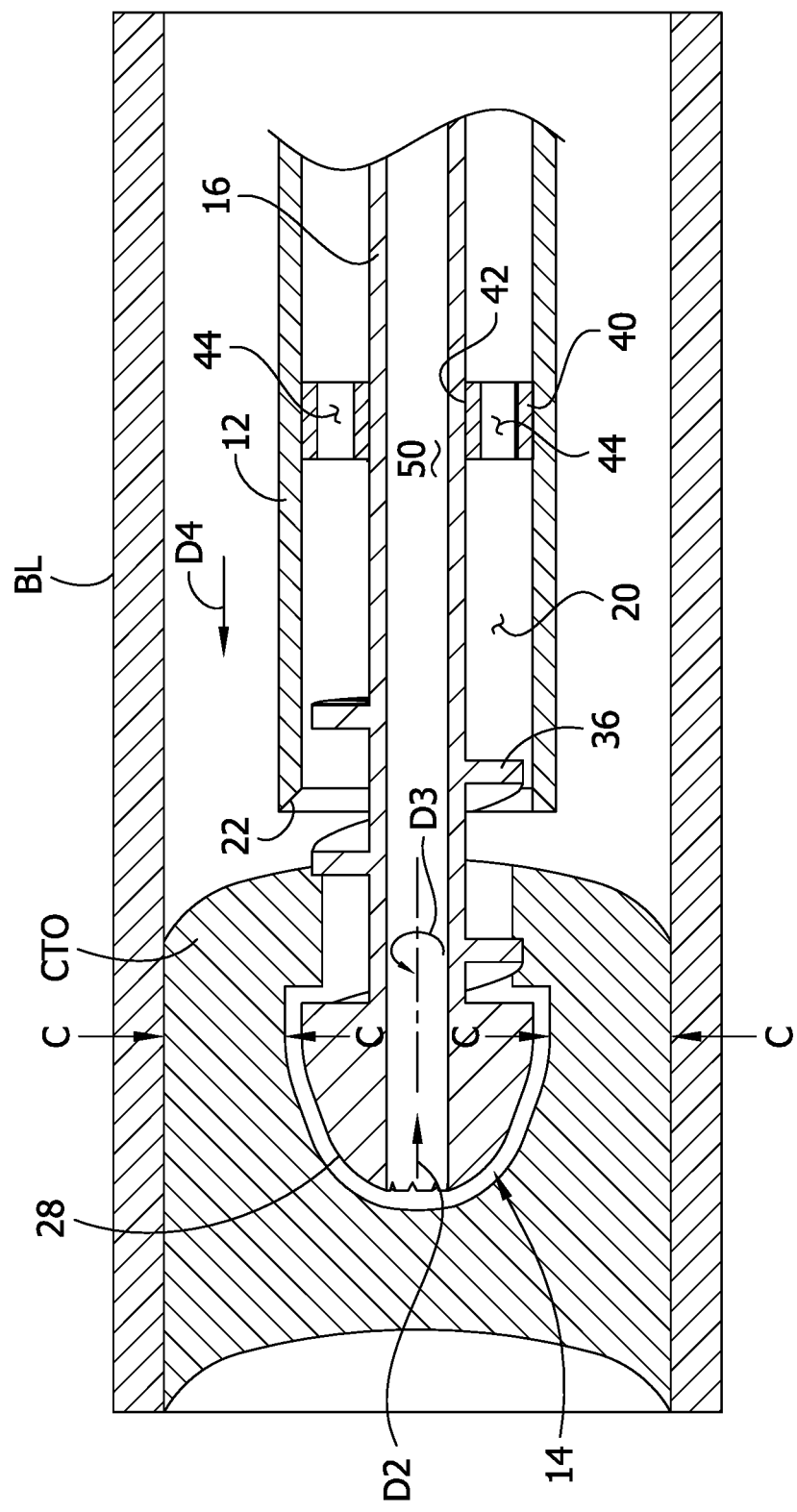
FIG. 4 is similar to FIG. 3, but with the tissue-removing head in the distal position and boring in the CTO.
Figure 5:
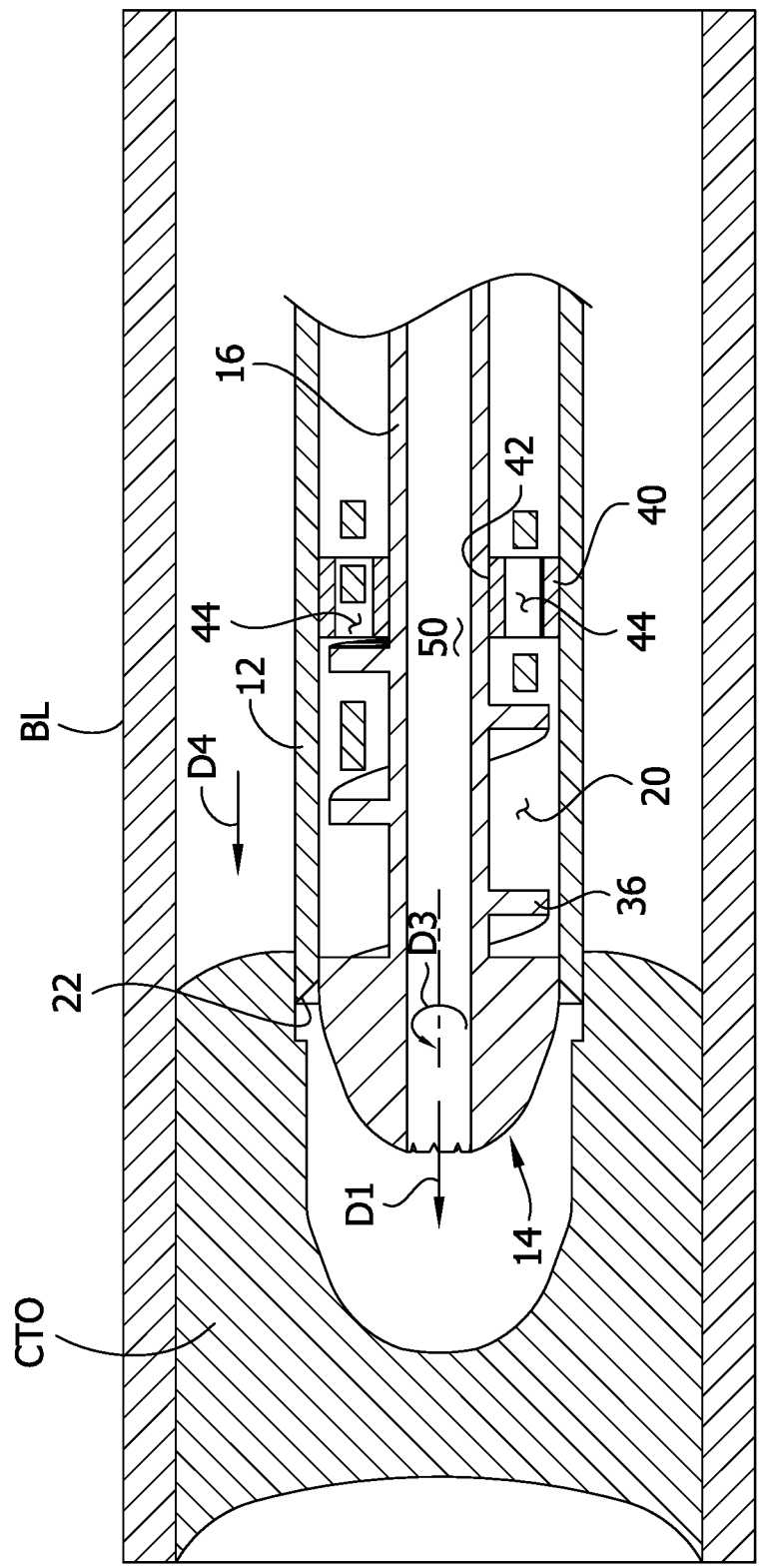
FIG. 5 is similar to FIG. 4, but with the tissue-removing head retracting back to the proximal position to shear tissue from the CTO.

Referring to FIGS. 3-5, the driveshaft 16 is rotatable and axially movable (so as to reciprocate) within the inner lumen 20 of the body 12. A distal end of driveshaft 16 is fixedly connected to the proximal end of the tissue-removing head 14 to impart rotation and reciprocating motion to the tissue-removing head. The driveshaft 16 may be formed separately from the tissue-removing head 14 or integrally formed therewith. The driveshaft 16 may be operatively connected to the tissue-removing head 14 in other ways suitable for imparting rotation to the tissue-removing head. The distal end portion of the driveshaft 16 includes a helical thread 36 (e.g., an Archimedes' blade) surrounding the longitudinal axis of the driveshaft. The illustrated thread 36 has a variable pitch, with the pitch being relatively coarse adjacent the distal end of the thread and fine (substantially flat) adjacent the proximal end. As explained below, during the tissue-removing operation the helical thread 36 functions as a tissue-transport mechanism to transport removed tissue proximally within the inner lumen 20 of the catheter body 12. The variable pitch of the thread 36 maximizes the tissue transport speed due to the coarse pitch at a distal portion of the thread, and facilitates grinding or breaking up of tissue due to the fine pitch at a proximal portion of the thread, as explained in more detail below. In other embodiments, the driveshaft may not include the thread 36.

Figure 6:
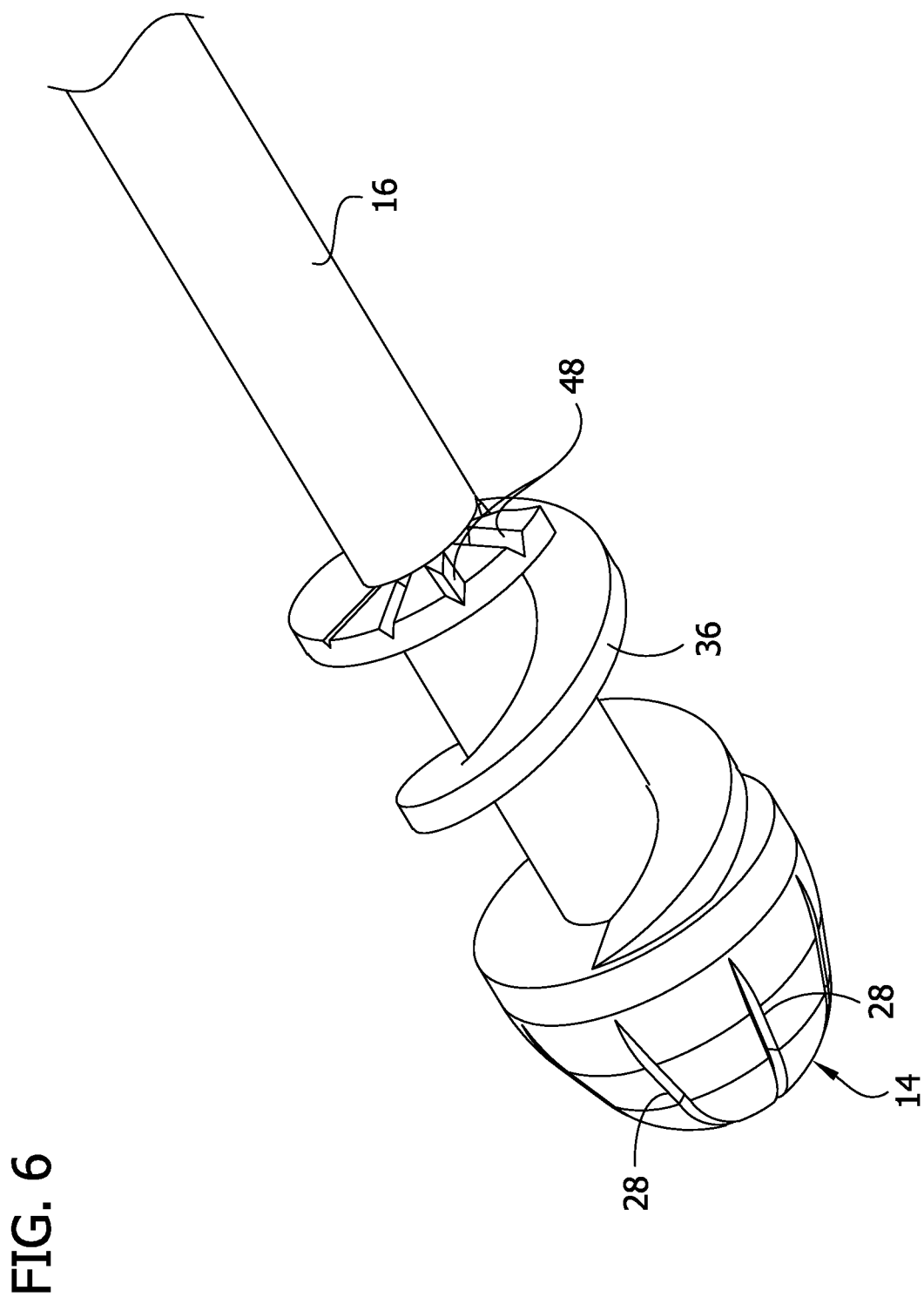
FIG. 6 is a perspective of the tissue-removing head and the driveshaft.
Figure 7:
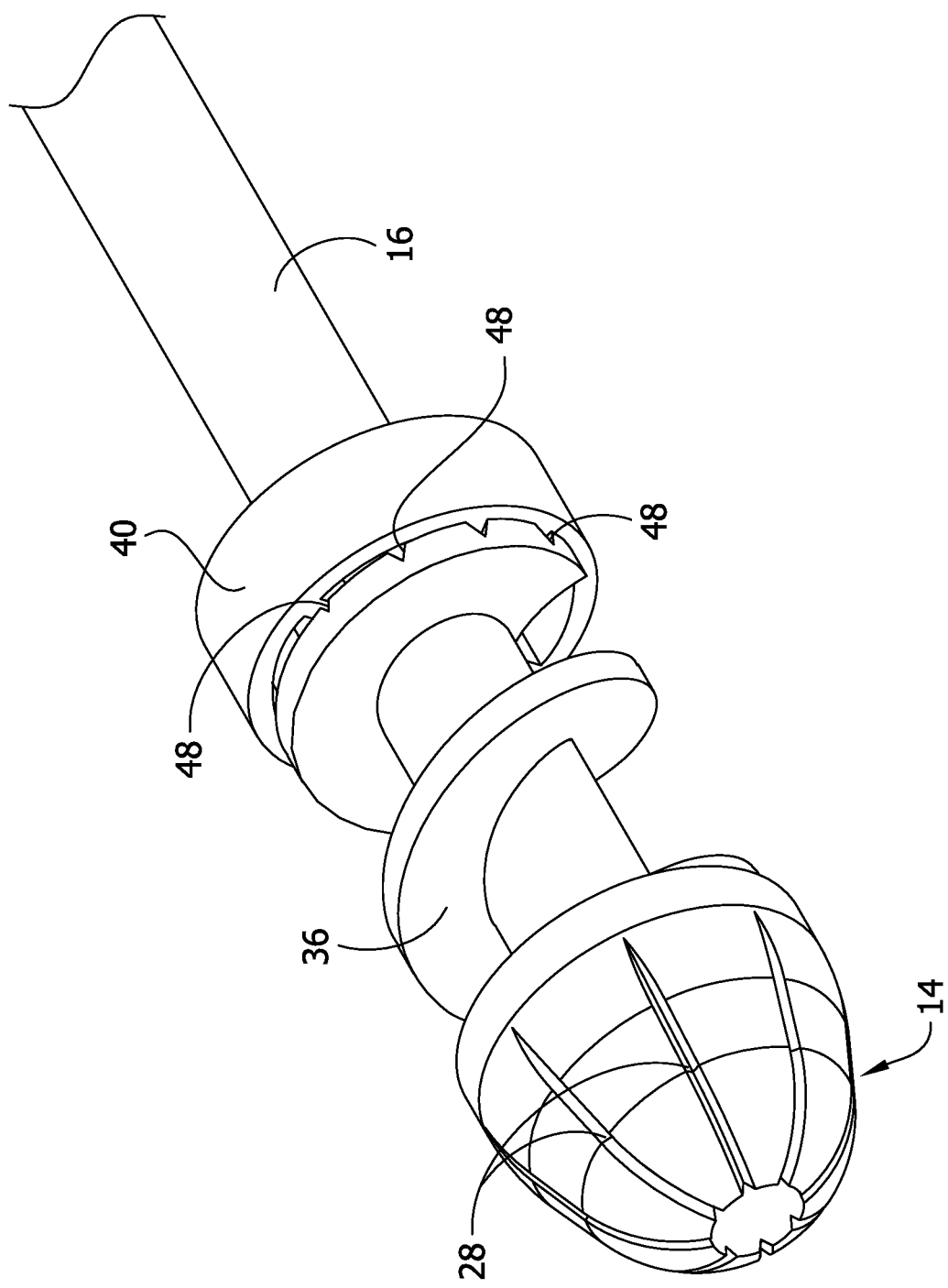
FIG. 7 is a perspective of the tissue-removing head, the driveshaft, and a driveshaft bushing.
Figure 8:
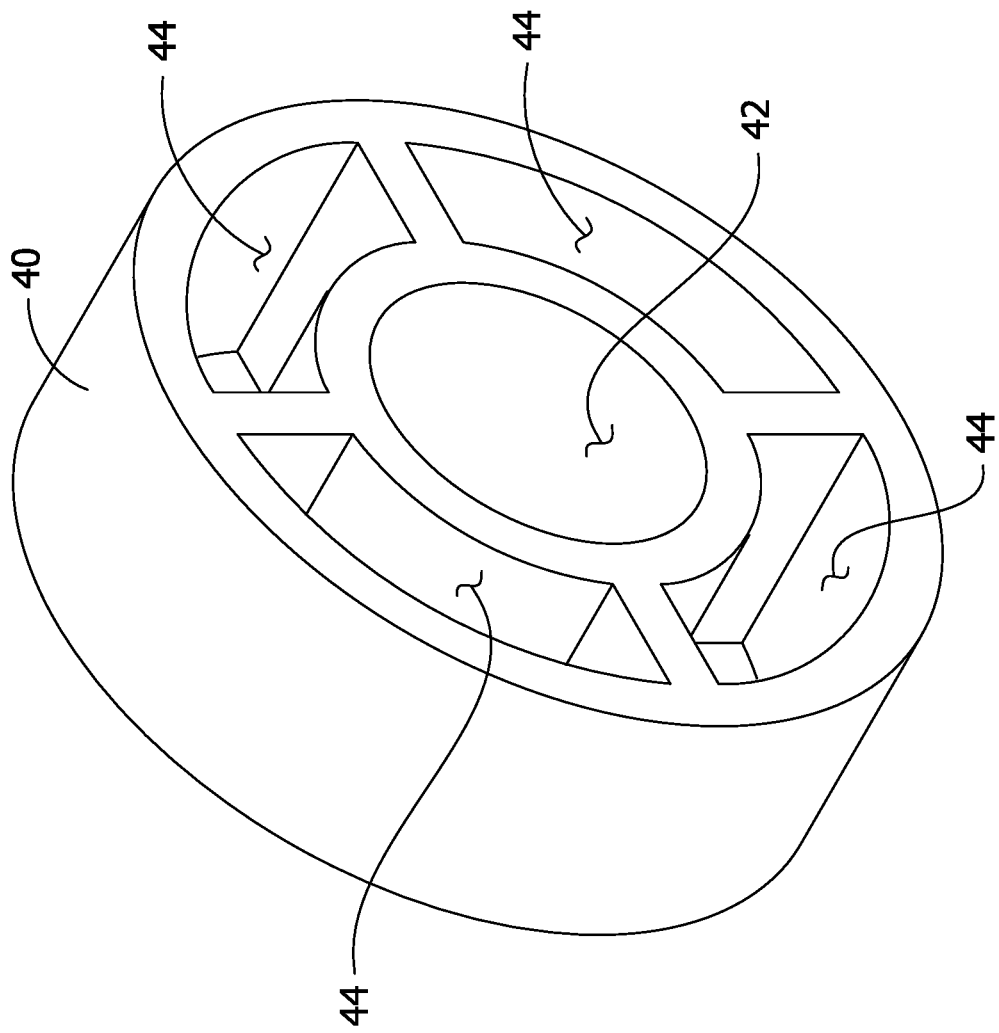
FIG. 8 is a perspective of the driveshaft bushing.

Referring still to FIGS. 3-5, in the illustrated embodiment, the driveshaft 16 is connected to the catheter body 12 via a bearing or driveshaft bushing 40 attached to the catheter body in the inner lumen 20. The illustrated driveshaft bushing 40 has a generally disk-shape defining a bearing opening 42 aligned axially with the catheter body 12, and tissue openings 44 radially outward of the bearing opening and spaced apart from one another around the bearing opening. The driveshaft 16 passes through the bearing opening 42 (e.g., a central bearing opening), which is sized and shaped snugly receive the driveshaft while at the same time allowing the driveshaft to rotate and move axially (i.e., reciprocate) relative to the bushing 40 and the catheter body 12. The tissue openings 44 are sized and shaped to receive removed tissue being transported proximally within the inner lumen 20 via the thread 36, as explained in more detail below. When the tissue-removing head 14 and the driveshaft 16 are in the distal position (see e.g., FIGS. 4 and 7), the proximal portion of the thread 36 is spaced axially from a distal face of the bushing 40 to define a space therebetween in the inner lumen 20. When the tissue-removing head 14 and the driveshaft 16 are in the proximal position (see e.g., FIG. 5), the proximal portion of the thread 36 is adjacent and/or flush against the distal face of the bushing 40. As shown in FIGS. 6 and 7, the proximal end portion of the thread 36 includes grooves 48 (or ribs) or other structures which, along with the fine pitch of the thread, facilitate shearing and breaking up of removed tissue within the space between the thread and the bushing 40, as explained in more detail below. The tissue openings 44 in the bushing 40 also facilitate shearing and breaking up of removed tissue. The bushing 40 may include additional structures to facilitate shearing and breaking up of removed tissue.

Referring to FIG. 1, a control handle or other control device 102, shown schematically, operatively connects to the proximal end of the catheter 10. The control handle 102 includes a housing and at least one actuator 104 in the housing for driving rotation and reciprocation of the driveshaft. In one example, the control handle 102 may include a rotary actuator 106 for rotating the driveshaft about the longitudinal axis and a linear actuator 108 for reciprocating the driveshaft along the longitudinal axis. The rotary and linear actuators 106, 108 may share an electric motor or prime mover, or the actuators may have separate dedicated motors.

Referring to FIG. 3, in one embodiment of a tissue-removing operation using the catheter 10, the distal end of the catheter is delivered to a target site within a body lumen BL. In one particular example, the body lumen BL is a vascular lumen (e.g., an artery) and the target site is tissue (e.g., plaque) forming a chronic total occlusion CTO. In one example, the catheter 10 may be delivered to the target site over a guidewire (not shown). The illustrated catheter 10 has a guidewire lumen 50 extending through the driveshaft and the tissue-removing head for receiving a guidewire. The catheter 10 may be delivered to the target site in other ways without departing from the scope of the present invention. At the target site, the catheter 10 can be activated using the control handle, such as by activating a control lever, button or other device to activate the at least one actuator. Upon activating the catheter, the driveshaft and the tissue-removing head both rotate about the head axis A and reciprocate along the head axis between the proximal and distal positions. Simultaneously with the activation of the catheter 10, the user may move the catheter body 12 distally toward the occlusion (as indicated by arrow D4).

As shown in FIG. 4, the tissue-removing head bores (or reams) into the occlusion CTO as it rotates and moves distally to the distal position. As the tissue-removing head is boring, the tissue is cut by the cutting edges of the flutes 28 of the tissue-removing head 14, and simultaneously, the tissue is elastically compressed radially between the tissue-removing head and the wall of the body lumen BL, as indicated by arrows C. When the tissue-removing head 14 passes distally beyond a portion of this radially compressed tissue, the tissue rebounds radially inwardly toward the driveshaft 16 and the thread 36. Because the thread 36 is simultaneously rotating, the thread may engage the rebounded tissue and pull the tissue both toward the driveshaft 16 and proximally toward the shearing blade 22 of the catheter body 12. Moreover, from the distal position, the tissue-removing head 14 and the thread 36 move proximally (as indicated by the arrow D2) to pull the rebounded tissue proximally. During this proximal movement of the tissue-removing head 14 and the driveshaft 16 toward the proximal position, the rebounded tissue is sheared off from the occlusion as the thread and/or the tissue-removing head move proximally past the cutting blade 22 within the inner lumen 20. In the illustrated embodiment, as shown in FIG. 5, at least a proximal portion of the tissue-removing head 14 passes into the opening of the shearing blade 22 to facilitate shearing of the tissue. The sheared off or removed tissue enters the inner lumen 20 of the catheter body 12.

Referring to FIG. 5, the removed tissue in the inner lumen 20 is transported proximally toward the bushing 40. When the driveshaft 16 is in the distal position, tissue being transported via the thread 36 enters the space in the inner lumen 20 between the proximal end portion of the thread and the distal face of the driveshaft bushing 40. As the driveshaft 16 moves proximally from the distal position (FIG. 4) to the proximal position, the proximal end portion of the thread 36 compresses the removed tissue against the distal face of the bushing 40. Rotation of the thread 36 simultaneously with the thread moving proximally to compress the removed tissue both shears the removed tissue, thereby breaking the tissue into smaller fragments, and forces the removed tissue through the tissue openings 44 of the bushing 40. In the illustrated embodiment, the removed tissue is stored in the inner lumen 20 of the catheter body 12 at a location proximal of the bushing 40.

This operation of simultaneously rotating and reciprocating the tissue-removing head 14, while moving the catheter 10 distally, facilitates boring (or reaming) of the tissue-removing head through the occlusion CTO. In particular, the catheter 10 continues the process of the tissue-removing head 14 entering tissue, the tissue compressing then rebounding around the proximal end of the tissue-removing head, the rebounded tissue being picked up by the thread 36 and then sheared off from the occlusion CTO when the tissue-removing head and the driveshaft 16 moved proximally. Moreover, the continued rotation of the driveshaft thread 36 and the shearing and compression of the removed tissue between the proximal end of the thread and the distal face of the bushing 40 breaks up the removed tissue and moves the tissue through the bushing where it is stored in the inner lumen 20.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter comprising:
a catheter body having opposite proximal and distal ends and an inner lumen;
an annular shearing blade secured to the distal end of the catheter body;
a drive shaft received in the inner lumen;
a tissue-removing head connected to the drive shaft at the distal end of the catheter body, wherein the tissue-removing head is configured to rotate about a head axis relative to the catheter body, and wherein the tissue-removing head is configured to reciprocate along the head axis relative to the catheter body between a proximal position, in which the tissue-removing head is adjacent the annular shearing blade, and a distal position, in which the tissue-removing head is spaced axially from the annular shearing blade; and
a rotary actuator connected to the drive shaft and configured to drive rotation of the tissue-removing head relative to the catheter body about the head axis; and
a linear actuator connected to the drive shaft and configured to drive repetitive reciprocation of the tissue-removing head along the head axis between the proximal position and the distal position;
wherein the rotary actuator and the linear actuator are configured to simultaneously drive the rotation and repetitive reciprocation of the tissue-removing head to facilitate repetitively boring the tissue-removing head through tissue and urging tissue proximally toward the annular shearing blade.

2. The tissue-removing catheter set forth in claim 1, wherein the driveshaft is rotatable about the catheter body and operatively connected to the tissue-removing head to impart rotation of the tissue-removing head about the head axis.

3. The tissue-removing catheter set forth in claim 2, wherein the driveshaft is reciprocatable along the catheter body and operatively connected to the tissue-removing head to impart reciprocation of the tissue-removing head along the head axis.

4. The tissue-removing catheter set forth in claim 2, wherein the driveshaft has a longitudinal axis and includes an external helical thread surrounding the longitudinal axis, wherein the external helical thread is configured to transport removed tissue proximally along the driveshaft and within the catheter body as the driveshaft rotates relative to the catheter body.

5. The tissue-removing catheter set forth in claim 4, wherein the external helical thread extends proximally along the longitudinal axis from adjacent the tissue-removing head.

6. The tissue-removing catheter set forth in claim 5, wherein the external helical thread has a variable pitch.

7. The tissue-removing catheter set forth in claim 6, wherein the variable pitch of the external helical thread is relatively coarse adjacent a distal end of the external helical thread and relatively fine adjacent a proximal end of the external helical thread.

8. The tissue-removing catheter set forth in claim 4, further comprising a driveshaft bushing received in the catheter body and defining a bearing opening extending through proximal and distal ends of the driveshaft bushing, wherein the driveshaft extends through the bearing opening.

9. The tissue-removing catheter set forth in claim 8, wherein the driveshaft bushing is fixedly attached to the catheter body.

10. The tissue-removing catheter set forth in claim 8, wherein the driveshaft bushing defines a tissue opening disposed radially outward from the bearing opening and extending through the proximal and distal ends of the driveshaft bushing, wherein the tissue opening is configured to allow removed tissue transported via the external helical thread to pass proximally therethrough.

11. The tissue-removing catheter set forth in claim 10, wherein tissue opening comprises a plurality of tissue openings spaced apart from one another around the bearing opening.

12. The tissue-removing catheter set forth in claim 10, wherein the external helical thread has a proximal end configured to abut the distal end of the driveshaft bearing when the tissue-removing head is in the proximal position.

13. The tissue-removing catheter set forth in claim 12, wherein the proximal end of the external helical thread includes at least one of grooves and ribs to facilitate shearing and breaking up of removed tissue between the proximal end of the external helical thread and the distal end of the driveshaft bearing.

14. The tissue-removing catheter set forth in claim 1, wherein the tissue-removing head has a generally conical shape that tapers distally.

15. The tissue-removing catheter set forth in claim 14, wherein the tissue-removing head defines a plurality of flutes extending from a distal end toward a proximal end of the tissue-removing head.

16. The tissue-removing catheter set forth in claim 15, wherein the flutes are spaced apart from one another around the head axis.

17. The tissue-removing catheter set forth in claim 14, wherein the tissue-removing head has an abrasive exterior surface.

18. The tissue-removing catheter set forth in claim 1, wherein the annular shearing blade surrounds a proximal end portion of the tissue-removing head when the tissue-removing head is in the proximal position.

19. A method of removing tissue from a body lumen, the method comprising:
  delivering a distal end of catheter body of a tissue-removing catheter to a target site within the body lumen, wherein the target site includes tissue-to-be-removed and wherein the catheter body has an inner lumen and the tissue-removing catheter comprises a drive shaft received in the inner lumen;
  rotating a tissue-removing head connected to the drive shaft at the distal end of the catheter body about a head axis;
  simultaneously with said rotating, linearly moving the tissue-removing head distally along the head axis from a proximal position, in which the tissue-removing head is adjacent an annular shearing blade at the distal end of the catheter body, and a distal position, in which the tissue-removing head is spaced axially from the annular shearing blade;
  boring into the tissue-to-be-removed using the tissue-removing head as the tissue-removing head simultaneously rotates and moves distally along the head axis to the distal position;
  retracting proximally, after said boring, the tissue-removing head from the distal portion to the proximal position; and
  urging tissue proximally toward the annular shearing blade using the tissue-removing head as the tissue-removing head is retracted proximally;
  wherein the tissue-removing catheter comprises a rotary actuator connected to the drive shaft and configured to drive the rotation of the tissue-removing head about the head axis and a linear actuator connected to the drive shaft and configured to repetitively drive the linear reciprocating movement the tissue-removing head distally and proximally along the head axis;
  wherein the rotary actuator and the linear actuator are configured to simultaneously drive the rotation and repetitive reciprocation of the tissue-removing head to facilitate repetitively boring the tissue-removing head through the tissue and urging tissue proximally toward the annular shearing blade.

20. The method of removing tissue from a body lumen set forth in claim 19, further comprising shearing, simultaneously with said urging tissue, the urged tissue using the annular shearing blade to remove the urged tissue from the body lumen.

21. A tissue-removing catheter comprising:
  a catheter body having opposite proximal and distal ends;
  an annular shearing blade secured to the distal end of the catheter body;
  a tissue-removing head at the distal end of the catheter body, wherein the tissue-removing head is configured to rotate about a head axis relative to the catheter body, and wherein the tissue-removing head is configured to reciprocate along the head axis relative to the catheter body between a proximal position, in which the tissue-removing head is adjacent the annular shearing blade, and a distal position, in which the tissue-removing head is spaced axially from the annular shearing blade; and
  at least one actuator configured to drive (i) rotation of the tissue-removing head relative to the catheter body about the head axis and (ii) reciprocation of the tissue-removing head along the head axis between the proximal position and the distal position to facilitate repetitively boring the tissue-removing head through tissue and urging tissue proximally toward the annular shearing blade,
  wherein the tissue-removing head has a generally conical shape that tapers distally,
  wherein the tissue-removing head defines a plurality of flutes extending from a distal end toward a proximal end of the tissue-removing head.

* * * * *